United States Patent
Sato

(10) Patent No.: US 12,427,213 B2
(45) Date of Patent: Sep. 30, 2025

(54) VEHICULAR SANITIZATION CONTROL DEVICE AND VEHICULAR SANITIZATION CONTROL SYSTEM

(71) Applicant: Yazaki Corporation, Tokyo (JP)

(72) Inventor: Kazuya Sato, Makinohara (JP)

(73) Assignee: YAZAKI CORPORATION, Tokyo (JP)

( * ) Notice: Subject to any disclaimer, the term of this patent is extended or adjusted under 35 U.S.C. 154(b) by 542 days.

(21) Appl. No.: 17/860,306

(22) Filed: Jul. 8, 2022

(65) Prior Publication Data
US 2023/0028755 A1 Jan. 26, 2023

(30) Foreign Application Priority Data
Jul. 26, 2021 (JP) .................. 2021-121842

(51) Int. Cl.
| | |
|---|---|
| *A61L 2/10* | (2006.01) |
| *A61L 2/24* | (2006.01) |
| *A61L 2/26* | (2006.01) |
| *B60R 16/033* | (2006.01) |
| *H02J 7/00* | (2006.01) |
| *H02J 7/35* | (2006.01) |
| *B60S 1/64* | (2006.01) |

(52) U.S. Cl.
CPC ................. *A61L 2/10* (2013.01); *A61L 2/24* (2013.01); *A61L 2/26* (2013.01); *B60R 16/033* (2013.01); *H02J 7/0048* (2020.01); *H02J 7/0068* (2013.01); *H02J 7/35* (2013.01); *A61L 2202/11* (2013.01); *A61L 2202/14* (2013.01); *A61L 2202/25* (2013.01); *B60S 1/64* (2013.01); *H02J 2300/24* (2020.01);

(58) Field of Classification Search
CPC ..... A61L 2/10; A61L 2/24; A61L 2/26; A61L 2202/11; A61L 2202/14; A61L 2202/25
See application file for complete search history.

(56) References Cited

U.S. PATENT DOCUMENTS

| | | | | |
|---|---|---|---|---|
| 9,124,109 | B2 * | 9/2015 | Lota | H02J 7/0048 |
| 9,339,571 | B2 * | 5/2016 | Bilenko | A61L 2/10 |
| 9,694,739 | B2 * | 7/2017 | Salter | F21V 19/0015 |
| 9,782,504 | B2 * | 10/2017 | Holub | H05B 47/115 |
| 9,855,353 | B1 * | 1/2018 | Stacy | A61L 2/10 |
| 10,183,084 | B2 * | 1/2019 | Cahan | A61L 2/24 |
| 10,301,806 | B2 * | 5/2019 | Childress | A61L 2/10 |
| 10,668,178 | B2 * | 6/2020 | Brockschmidt | A61L 2/24 |

(Continued)

FOREIGN PATENT DOCUMENTS

| | | |
|---|---|---|
| CN | 111674237 A | 9/2020 |
| CN | 113082238 A | 7/2021 |

(Continued)

*Primary Examiner* — Sean M Luck
(74) *Attorney, Agent, or Firm* — Sughrue Mion, PLLC

(57) ABSTRACT

A vehicular sanitization control device includes a rechargeable internal power source, a deep ultraviolet light source, a first display light source configured to display an operating state of the deep ultraviolet light source, a second display light source configured to display a state of charge of the internal power source, and a control unit configured to control a power supplied to the deep ultraviolet light source, a charging operation of the internal power source, and displays of the first display light source and the second display light source, respectively.

8 Claims, 3 Drawing Sheets

(56) References Cited

U.S. PATENT DOCUMENTS

| | | | |
|---|---|---|---|
| 10,702,618 B2* | 7/2020 | Callahan | A61L 2/24 |
| 10,918,749 B2* | 2/2021 | Hatti | B64F 5/30 |
| 2007/0053188 A1* | 3/2007 | New | B60Q 3/43 |
| | | | 362/276 |
| 2008/0110485 A1* | 5/2008 | Vasilantone | H02S 99/00 |
| | | | 136/243 |
| 2012/0176241 A1* | 7/2012 | Pasch | A61L 2/10 |
| | | | 250/492.1 |
| 2014/0183377 A1* | 7/2014 | Bettles | A61L 2/10 |
| | | | 250/455.11 |
| 2014/0316607 A1* | 10/2014 | Le | B60R 16/037 |
| | | | 701/1 |
| 2015/0137747 A1* | 5/2015 | Salter | A61L 2/10 |
| | | | 320/108 |
| 2015/0190538 A1* | 7/2015 | Olvera | A61L 2/24 |
| | | | 250/455.11 |
| 2015/0273092 A1 | 10/2015 | Holub et al. | |
| 2016/0136314 A1* | 5/2016 | Kreitenberg | A61L 2/10 |
| | | | 250/492.1 |
| 2017/0129396 A1* | 5/2017 | Salter | A61L 2/10 |
| 2018/0193505 A1* | 7/2018 | Liao | A61L 2/10 |
| 2018/0229694 A1* | 8/2018 | Salter | B60J 7/043 |
| 2018/0244160 A1* | 8/2018 | Bullen | H02K 11/0094 |
| 2019/0076558 A1* | 3/2019 | Zhang-Miske | B60N 2/0029 |
| 2019/0091738 A1* | 3/2019 | Chen | B60H 1/00742 |
| 2020/0061223 A1* | 2/2020 | Hallack | A61L 2/24 |
| 2020/0142362 A1* | 5/2020 | Alessi | G05B 13/024 |
| 2020/0238790 A1 | 7/2020 | Nishiyama et al. | |
| 2020/0307472 A1* | 10/2020 | Line | B60R 15/00 |
| 2020/0331611 A1* | 10/2020 | Hack | B60Q 3/47 |
| 2020/0338220 A1* | 10/2020 | Kim | B60H 1/00814 |
| 2022/0031880 A1 | 2/2022 | Hwang et al. | |

FOREIGN PATENT DOCUMENTS

| | | |
|---|---|---|
| JP | 2000-140087 A | 5/2000 |
| JP | 2004-413 A | 1/2004 |
| JP | 2006-341759 A | 12/2006 |
| JP | 2010-95227 A | 4/2010 |
| JP | 2017-225629 A | 12/2017 |
| JP | 2020-121598 A | 8/2020 |
| KR | 10-2021-0005765 A | 1/2021 |
| KR | 10-2249536 B1 | 5/2021 |
| WO | 2017/204774 A1 | 11/2017 |

* cited by examiner

VEHICULAR SANITIZATION CONTROL DEVICE AND VEHICULAR SANITIZATION CONTROL SYSTEM

CROSS-REFERENCE TO RELATED APPLICATIONS

This application is based on and claims priority under 35 USC 119 from Japanese Patent Application No. 2021-121842 filed on Jul. 26, 2021, the contents of which are incorporated herein by reference.

TECHNICAL FIELD

The present disclosure relates to a vehicular sanitization control device and a vehicular sanitization control system.

BACKGROUND ART

In recent years, in an environment where automobiles are used, a new usage form such as car sharing is being introduced. In such a usage form, an unspecified number or specified number of users take turns in one common vehicle.

In a situation where one vehicle is shared by many users as in the above case, it is necessary to maintain cleanliness of a vehicle interior environment. If the vehicle interior environment is clean, it will be easier for each user to use this vehicle, which will lead to promotion of the car sharing. However, in order to maintain the vehicle interior environment at all times, it is generally necessary to perform a vehicle interior cleaning work, and a running cost for maintenance is expected to increase. Further, a time period where the vehicle cannot be used due to cleaning inside the vehicle is generated.

Meanwhile, JP-A-2006-341759 discloses a vehicle sanitizer that can blow out sanitizing ions to effectively sanitize an inside of a vehicle.

For example, in a case of the sanitization technique such as JP-A-2006-341759, the vehicle can be sanitized while being used by a user, and thus, there is a possibility that a time required for cleaning an inside of the vehicle can be saved in a usage form where various users take turns to use the common vehicle, such as car sharing. The same applies not only to the car sharing but also to a case of using, for example, a taxi vehicle.

However, in a case of the sanitization technique using ions or the like, for example, an ability to inactivate coronavirus may be poor or sanitization may take time, and thus it is unclear whether a sufficient effect can actually be obtained.

In addition, in the case of the sanitization technique such as JP-A-2006-341759, it is necessary to supply, from a battery for the vehicle, a power consumed by the vehicle sanitizer. Therefore, if sanitization is attempted during a time period where the vehicle is not in use, such as the vehicle is parked, there is a concern that a running out of a battery (a dead battery) of the vehicle may occur.

In addition, if the vehicle is equipped with only one sanitizer, it is difficult to sanitize every corner inside the vehicle. Further, when a plurality of sanitizers are mounted on the vehicle, a power consumption increases when these sanitizers are operated at the same time, so that a possibility of the dead battery of the vehicle further increases.

In the case of the car sharing or the like, each user who attempts to use the vehicle cannot know whether the vehicle is maintained in a clean state, and thus, it is difficult to obtain a sense of security when riding.

SUMMARY OF INVENTION

The present disclosure has been made in view of the above circumstances, and an object of the present disclosure is to provide a vehicular sanitization control device that easily keeps a vehicle, which may be used by various users, always clean, and hardly generate a dead battery of the vehicle.

In order to achieve the above-mentioned object, the vehicular sanitization control device and a vehicular sanitization control system according to the present disclosure respectively have the following characteristics.

According to an aspect of the present disclosure, there is provided A vehicular sanitization control device, including: a rechargeable internal power source, a deep ultraviolet light source, a first display light source configured to display an operating state of the deep ultraviolet light source, a second display light source configured to display a state of charge of the internal power source, and a control unit configured to control a power supplied to the deep ultraviolet light source, a charging operation of the internal power source, and displays of the first display light source and the second display light source, respectively.

According to an aspect of the present disclosure, there is provided A vehicular sanitization control system, including the vehicular sanitization control device, a vehicular battery mounted on a vehicle, and a solar panel mounted on the vehicle, in which the control unit switches a supply source of a power supplied to the deep ultraviolet light source to the vehicular battery in a case that an ignition of the vehicle is in an on state, and switches the supply source of the power supplied to the deep ultraviolet light source to the solar panel in a case that the ignition of the vehicle is in an off state.

According to the vehicular sanitization control device and the vehicular sanitization control system of the present disclosure, by sanitizing a vehicle that may be used by various users, the vehicle becomes easy to be maintained in a clean state at all times. In addition, since a power of an internal power source which is different from the battery for the vehicle can be used, a running out of the battery of the vehicle is hard to occur.

The present disclosure has been briefly described above. Further, details of the present disclosure will be clarified by reading through embodiments for carrying out the invention (hereinafter, referred to as "embodiment".) described below with reference to the accompanying drawings.

DESCRIPTION OF EMBODIMENTS

Specific embodiments according to the present disclosure will be described below with reference to the drawings.

Figure 1:
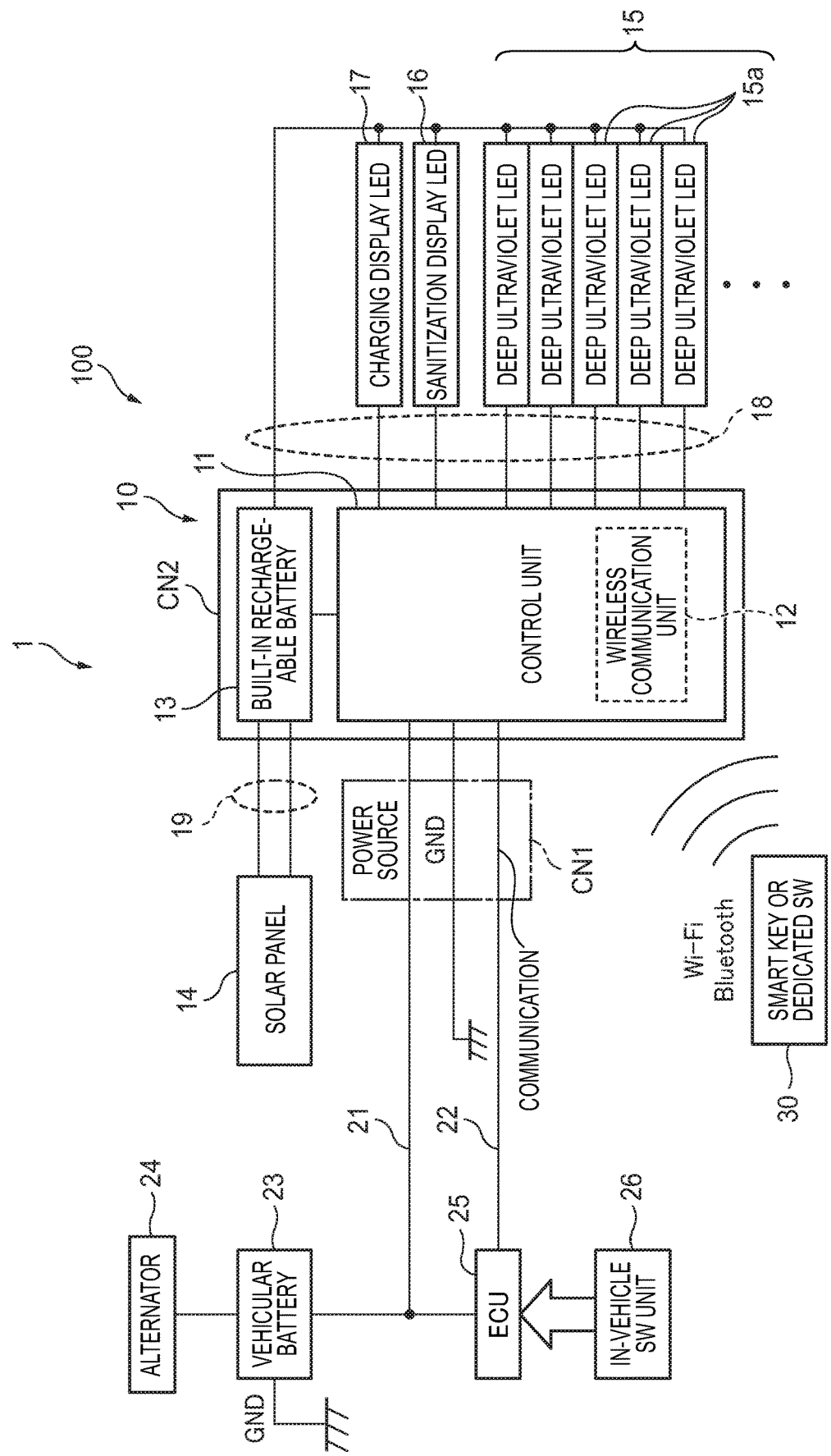
FIG. 1 is an electric circuit diagram showing a configuration example of a vehicular sanitization control device according to an embodiment of the present disclosure.

FIG. 1 is an electric circuit diagram showing a configuration example of a vehicular sanitization control device 100 according to an embodiment of the present disclosure.

The vehicular sanitization control device 100 shown in FIG. 1 implements a sanitization function particularly suitable to a case of being mounted on a vehicle used by an unspecified number of users, such as a vehicle for car sharing or a taxi vehicle, and constitutes a vehicular sanitization control system 1 together with a vehicular battery 23, an ECU 25, and an in-vehicle switch unit 26 mounted on the vehicle.

The vehicular sanitization control device 100 shown in FIG. 1 includes a sanitization unit 15. The sanitization unit 15 includes a plurality of deep ultraviolet LEDs (light emitting diodes) 15a. Each deep ultraviolet LED 15a is a light source having a light emitting property capable of emitting a deep ultraviolet light having a wavelength of, for example, 222 [nm]. It is known that the deep ultraviolet light having such a wavelength can inactivate viruses and bacteria by irradiation for several minutes, for example, and have almost no effect when emitted to a human body. Therefore, the deep ultraviolet light is suitable for a use for a purpose of sanitizing an inside of the vehicle.

For example, in a case of the vehicle for a purpose of the car sharing, it is desirable to sanitize an entire area inside the vehicle. However, a range in which the deep ultraviolet light is emitted by one deep ultraviolet LED 15a is limited to only a part of the inside of the vehicle. Therefore, it is important to dispersedly provide the plurality of deep ultraviolet lights 15a in various parts inside the vehicle such that each deep ultraviolet LED 15a irradiates different regions with the deep ultraviolet light.

Therefore, for example, it is assumed that the deep ultraviolet LEDs 15a are installed at a ceiling above seats inside the vehicle respectively to emit the deep ultraviolet light toward the seats. It is also assumed that the deep ultraviolet LEDs 15a are installed at doors of the vehicle respectively to emit the deep ultraviolet light toward the seats. Furthermore, it is assumed that the deep ultraviolet LED 15a is installed at a portion such as a ceiling of a luggage compartment.

In an actual vehicle, a lamp such as an LED for illuminating with a visible light is usually installed at a portion such as a ceiling above the seats or a door. In addition, the lamp such as the LED that can emit the visible light is often installed for decorative lighting. Therefore, the deep ultraviolet LED 15a is installed at each of these portions in a state of being adjacent to the lamp such as a light source of a visible light. Accordingly, it is no need to secure a new installation space for the deep ultraviolet LED 15a, and the sanitization over the entire area inside the vehicle can be achieved easily.

The vehicular sanitization control device 100 includes a sanitization display LED 16 and a charging display LED 17. The sanitization display LED 16 is designed to display an operating status of the sanitization unit 15 in a state where the user can visually recognize the operating status. The charging display LED 17 displays a state of charge of a built-in rechargeable battery 13 in a state where the user can visually recognize the state of charge.

Functions of the sanitization display LED 16 and the charging display LED 17 can be implemented only by changing controls of light sources of a general lighting device and a decorative lighting device mounted on the vehicle in advance. When using these light sources, it is unnecessary to newly add the sanitization display LED 16 and the charging display LED 17.

In the present embodiment, a device capable of emitting a blue light is adopted as the sanitization display LED 16, and a full-color display device capable of selectively emitting a green light, a yellow light, and a red light is adopted as the charging display LED 17.

In the example shown in FIG. 1, the vehicular sanitization control device 100 includes a connector portion 10. The deep ultraviolet LEDs 15a of the sanitization unit 15, the sanitization display LED 16, and the charging display LED 17 are connected to the connector portion 10 via a wire harness 18. The connector portion 10 includes a control unit 11, a wireless communication unit 12, and the built-in rechargeable battery 13. The connector portion 10 is housed in a housing of a connector CN2.

A connector CN1 and the connector CN2 in FIG. 1 form a pair, are configured to be fitted to each other, and are configured to be removable.

The control unit 11 is implemented by, for example, an electronic circuit having a microcomputer as a main body, and has a wired communication function. The control unit 11 can also perform wireless communication by using the wireless communication unit 12. The microcomputer of the control unit 11 can execute various controls described later by executing a pre-built-in program.

The wireless communication unit 12 is a communication module that enables wireless communication corresponding to a standard communication specification such as Wi-Fi (registered trademark) or Bluetooth (registered trademark), and is capable of relatively short-range wireless communication. In the present embodiment, the wireless communication unit 12 is used to enable communication with a smart key 30.

The built-in rechargeable battery 13 is housed in a housing of the connector CN2 and is removably attached to the housing of the connector CN2. The built-in rechargeable battery 13 is implemented by, for example, a lithium ion battery. The built-in rechargeable battery 13 is connected to the control unit 11, the sanitization unit 15, the sanitization display LED 16, and the charging display LED 17 in a state where a source power can be supplied. A solar panel 14 is connected to a charging circuit of the built-in rechargeable battery 13 via a wire harness 19.

The solar panel 14 is installed on a part of the vehicle that is easily exposed to sunlight under normal conditions, such as on a roof of a vehicle body, an upper part of a dashboard, and an upper part of each of the doors. The solar panel 14 has a sufficient power generation capacity to charge the built-in rechargeable battery 13.

The connectors CN1 and CN2 connected to each other house electric wires assigned to a power source, ground (GND), and communication.

In the example shown in FIG. 1, the vehicle is mounted with the vehicular battery 23 as a main power source. An alternator 24 is connected to an input side of the vehicular battery 23. A case of a vehicle having a built-in high-voltage power source, such as an electric vehicle and a plug-in hybrid vehicle, an output of the high-voltage power source, instead of the alternator 24, is connected to the vehicular battery 23 via a predetermined DC/DC converter.

The source power on the vehicle side output by the vehicular battery 23 is supplied to the connector portion 10 via a power source line 21 and the connectors CN1 and CN2.

Inside the vehicle, various switches (SW) are installed at positions that can be operated by a user such as a driver. These switches are contained in the in-vehicle switch unit 26 shown in FIG. 1.

The electronic control unit (ECU) 25 mounted on the vehicle can read a state of each switch of the in-vehicle switch unit 26. In a power input of the ECU 25, the power is supplied from the vehicular battery 23.

The ECU 25 has a communication function corresponding to a communication specification for vehicles such as a controller area network (CAN), and can communicate with another ECU or the like via a communication line 22. The communication line 22 of the ECU 25 is wiredly connected to the control unit 11 via the connectors CN1 and CN2.

The smart key 30 has a function for locking or unlocking a door lock by the wireless communication, similar to a smart key for a general vehicle. The smart key 30 shown in FIG. 1 also includes a switch to which a function of switching a sanitizing operation on and off in the vehicular sanitization control device 100 is assigned.

The smart key 30 has a built-in communication module that enables wireless communication corresponding to specifications such as Wi-Fi and Bluetooth, and can perform the wireless communication with the wireless communication unit 12 of the vehicular sanitization control device 100. Instead of the smart key 30, a dedicated remote control switch specialized only for the on and off operation function of the sanitizing operation may be used.

Figure 2:
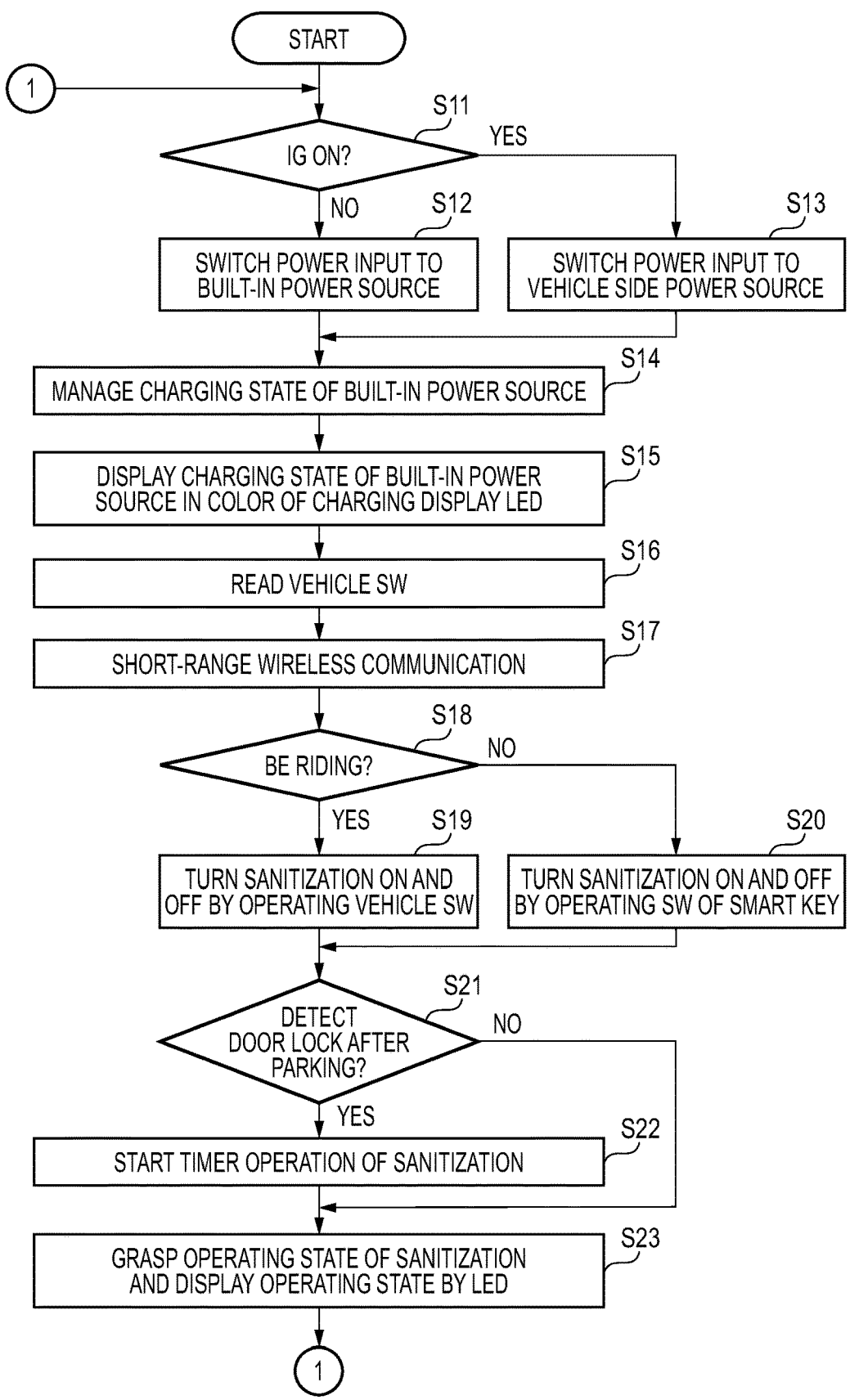
FIG. 2 is a flowchart showing main operations of the vehicular sanitization control device.

FIG. 2 is a flowchart showing main operations of the vehicular sanitization control device 100. That is, the control unit 11 performs a control shown in FIG. 2. The operations in FIG. 2 will be described below.

The control unit 11 identifies an ignition (IG) state of the vehicle with S11. The control unit 11 can identify an on state and an off state of IG by communicating with the ECU 25 via the communication line 22.

When the IG is in the off state, the control unit 11 proceeds from S11 to S12, and switches power inputs of the control unit 11 itself, the wireless communication unit 12, the sanitization unit 15, the sanitization display LED 16, and the charging display LED 17 to the output of the built-in rechargeable battery 13. That means, the power source supplying the power to the control unit 11, the wireless communication unit 12, the sanitization unit 15, the sanitization display LED 16, and the charging display LED 17 is switched to the built-in rechargeable battery 13.

When IG is in the on state, the control unit 11 proceeds from S11 to S13, and switches the power inputs of the control unit 11 itself, the wireless communication unit 12, the sanitization unit 15, the sanitization display LED 16, and the charging display LED 17 to a vehicle side, that is, a power source line 21 connected to the vehicular battery 23.

The control unit 11 manages a state of charge and a storage state of the built-in rechargeable battery 13 in S14. For example, an actual state of charge of the built-in rechargeable battery 13 can be grasped by monitoring values of a charge current, a discharge current, an output voltage, and the like of the built-in rechargeable battery 13, and changes of the values. Next, in S15, the control unit 11 reflects the state of charge and the storage state of the built-in rechargeable battery 13 by a display of the charging display LED 1. In the present embodiment, a difference in the state of charge or the storage state is shown by a difference in an emission color of the charging display LED 17.

In S16, the control unit 11 communicates with the ECU 25 via the communication line 22, and reads the state of each switch of the in-vehicle switch unit 26. Next, in S17, the control unit 11 uses the wireless communication unit 12 to perform a relatively short-range wireless communication with the smart key 30.

In S18, the control unit 11 determines whether the user such as a driver is in the own vehicle. For example, whether the user is in the own vehicle can be determined by detecting whether each seat is seated or whether the smart key 30 is present in the vicinity of the seat of the driver.

When the user is in the own vehicle, the control unit 11 switches the sanitization function on and off according to an operation status of the in-vehicle switch contained in the in-vehicle switch unit 26 (S19). That is, when the sanitization function is turned on, a source power is supplied to each deep ultraviolet LED 15*a* of the sanitization unit 15 such that the deep ultraviolet light is emitted. In addition, when the sanitization function is turned off, the source power supply to all the deep ultraviolet LEDs 15*a* of the sanitization unit 15 is cut off. Meanwhile, when the user is outside the own vehicle, the control unit 11 switches the sanitization function on and off according to a switch operation status in the smart key 30 (S20). Next, in S21, the control unit 11 determines whether a door locked state is detected after the own vehicle is parked. The operation proceeds from S21 to S22, for example, if a parking brake is in an on state, the IG is off, and the door is further locked.

In S22, the control unit 11 starts a timer operation of the sanitizing operation. That is, the control unit 11 switches the sanitization function of the sanitization unit 15 on, and starts a time counting operation of a sanitization timer for automatically stopping the sanitizing operation. After that, when a certain period of time previously assigned to the sanitization timer elapses, the sanitization function of the sanitization unit 15 is switched off.

Therefore, in the parked state after any user uses the vehicle, the sanitizing operation is surely performed for a certain period of time by the timer operation. Therefore, when a next user uses this vehicle, the user may be invited in a clean state where the inside of the vehicle is sanitized.

The control unit 11 grasps the operating state of the sanitization unit 15 in S23 and reflects the state by the display of the sanitization display LED 16. That is, even if each deep ultraviolet LED 15*a* of the sanitization unit 15 is in a light emitting state, the user cannot visually recognize the deep ultraviolet light, so that the user cannot know the state only by operating the sanitization unit 15. However, by displaying the sanitization display LED 16 in conjunction with the sanitizing operation, the user can confirm whether the sanitization function is operating.

Figure 3:
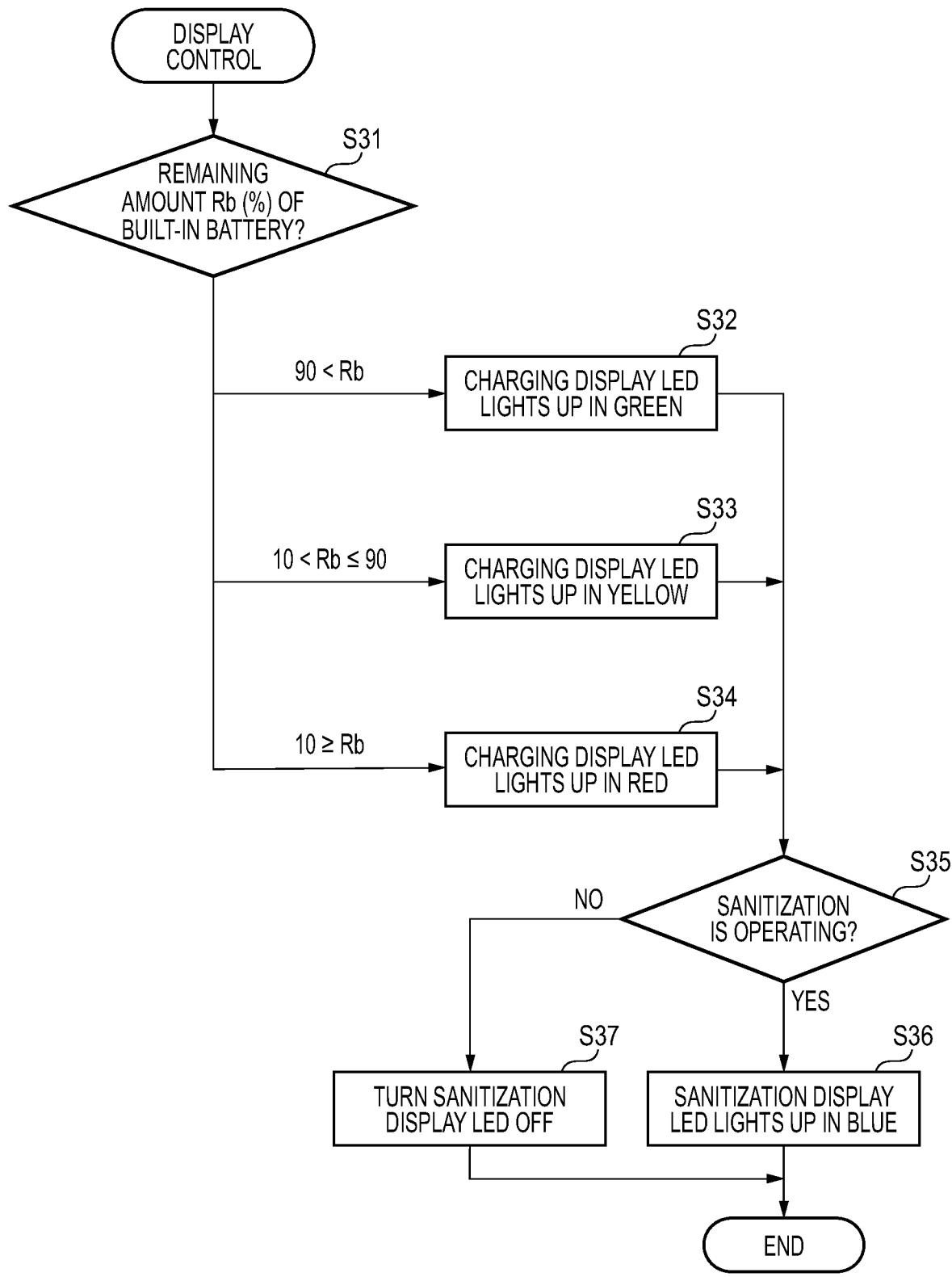
FIG. 3 is a flowchart showing details of a part of the operations shown in FIG. 2.

FIG. 3 is a flowchart showing details of a part of the operations shown in FIG. 2. That is, FIG. 3 shows the details of the operations corresponding to the steps S15 and S23 shown in FIG. 2. The operations illustrated in FIG. 3 will be described below.

The control unit 11 compares a remaining amount Rb (%) of power stored in the built-in rechargeable battery 13 with predetermined thresholds of 10(%) and 90(%), respectively. If "90<Rb", the operation proceeds to S32, if "10<Rb≤90", the operation proceeds to S33, and if "10≥Rb", the operation proceeds to S34, The remaining amount Rb can be estimated by calculation based on an amount of a change in a voltage or a power consumed from a reference state, for example, a state where the built-in rechargeable battery 13 is fully charged (100%).

If "90<Rb", the control unit 11 controls the display such that the charging display LED 17 lights up in green. If "10<Rb≤90", the display is controlled such that the charging display LED 17 lights up in yellow. If "10≥Rb", the display is controlled such that the charging display LED 17 lights up in red.

Meanwhile, in S35, the control unit 11 determines whether the sanitization unit 15 is operating. If one or more deep ultraviolet LEDs 15*a* are being lighted (being energized), the sanitization function is regarded as operating, and then the operation proceeds to S36, and the sanitization display LED 16 is controlled to be lighted in blue. That is, the power is supplied to the sanitization display LED 16.

If all the deep ultraviolet LEDs 15*a* of the sanitization unit 15 are turned off (non-energized state), the control unit 11 regards that the sanitization function is in a non-operating state, and then proceeds to S37, and turns off the sanitization display LED 16.

As described above, in the vehicular sanitization control device 100 according to the present embodiment, the sanitization is performed by using the deep ultraviolet LED 15*a*, so that the inside of the vehicle including viruses and the like can be efficiently sanitized. Moreover, if a deep ultraviolet light having a specific wavelength that does not affect the human body is used, the sanitization can also be performed when the user rides on the vehicle. Therefore, in a case where a general vehicle is shared and used by an unspecified number of users by car sharing, or a case where a taxi is used, it is possible to always entertain each user in a clean state when the user rides on the vehicle, and no special cleaning work is required.

Although the deep ultraviolet light cannot be visually recognized, the deep ultraviolet light is displayed by the sanitization display LED 16 when the sanitization function of the vehicular sanitization control device 100 is operating, and thus, the user of the vehicle can easily recognize the operation of the sanitization function.

Further, since the sanitization can be performed by using the power of the built-in rechargeable battery 13, the sanitization can be performed without causing a dead battery of the vehicular battery 23 even when an engine is stopped as in the case of parking. By using the solar panel 14, the built-in rechargeable battery 13 can be charged without affecting a storage capacity of the vehicular battery 23.

In addition, by linking with a wireless remote controller such as the smart key 30, even when the user of the vehicle is outside the vehicle, operations such as on and off for the sanitization function can be performed. Further, by housing the control unit 11 and the built-in rechargeable battery 13 in the housing of the connector CN2, it becomes easy to retrofit a general vehicle with a function of the vehicular sanitization control device 100 as an option.

The present disclosure is not limited to the above-described embodiments, and can be appropriately modified, improved, and the like. In addition, the material, shape, size, number, arrangement location, and the like of each component in the above-described embodiments are optional and are not limited as long as the present disclosure can be achieved.

Here, characteristics of the vehicular sanitization control device and the vehicular sanitization control system according to the embodiments of the present disclosure will be briefly summarized in the following [1] to [6].

[1] A vehicular sanitization control device (100), including:
a rechargeable internal power source (built-in rechargeable battery 13);
a deep ultraviolet light source (deep ultraviolet LEDs 15*a*);
a first display light source (sanitization display LED 16) configured to display an operating state of the deep ultraviolet light source;
a second display light source (charging display LED 17) configured to display a state of charge of the internal power source; and
a control unit (11) configured to control a power supplied to the deep ultraviolet light source, a charging operation of the internal power source, and displays of the first display light source and the second display light source, respectively.

According to the vehicular sanitization control device having the configuration in the above [1], the source power is supplied to the deep ultraviolet light source, and then a deep ultraviolet light can be generated in a vehicle to perform sanitization. In particular, by using the deep ultraviolet light, it becomes possible to inactivate viruses and the like in a relatively short time without adversely affecting a human body. In addition, since the source power can be supplied from the internal power source to the deep ultraviolet light source, a dead battery of the vehicle can be prevented even when the sanitization is performed while the vehicle is parked. In addition, although the deep ultraviolet light is generated invisible, by using the first display light source to display the operating state of the deep ultraviolet light source, a user of the vehicle can be informed that a clean environment is maintained by the sanitization. Therefore, even in a situation where an unspecified number of users take turns to use one vehicle, each user can recognize that an inside of the vehicle is clean, and thus, a useful function of entertaining the user of the vehicle can be realized. In addition, a state of the internal power source can be notified to the user by the second display light source.

[2] The vehicular sanitization control device according to above [1], including: a solar panel (14) mounted on a vehicle, in which
the solar panel is configured to be connected to a charging circuit of the internal power source.

According to the vehicular sanitization control device having the configuration in the above [2], even when a stored power of the internal power source is low, charging can be performed at any time as long as the vehicle is exposed to a light such as sunlight from the outside. Therefore, for example, even when the sanitization function is operated in a situation where the vehicle has been parked for a long time, the internal power source can be prevented from running out of the stored power.

[3] The vehicular sanitization control device according to the above [1] or [2], in which
the control unit includes a wireless communication unit (12) configured to perform wireless communication with a wireless remote control unit (smart key 30), and
in response to a change in a state of the wireless remote control unit, the control unit controls an operation of supplying the power to the deep ultraviolet light source (S20).

According to the vehicular sanitization control device having the configuration of the above [3], a user uses the wireless remote control unit, so that the user can switch a sanitization function on and off even when the user is outside the vehicle.

[4] The vehicular sanitization control device according to any one of the above [1] to [3], in which
the control unit switches a supply source of the power supplied to the deep ultraviolet light source in response to an on state and an off state of an ignition of a vehicle (S11 to S13).

According to the vehicular sanitization control device having the configuration in the above [4], for example, when an engine of the vehicle is stopped, the supply source of the power supplied to the deep ultraviolet light source is switched to the internal power source, so that the dead battery of the vehicular battery can be prevented. For example, when the engine of the vehicle is operating and a vehicular generator or the like can be used, a source power consumption from the internal power source can be suppressed by switching the supply source of the power to an output of the vehicular battery or the like having a sufficient capacity.

[5] The vehicular sanitization control device according to any one of the above [1] to [4], in which
the control unit includes a timer configured to limit a length of a time of a sanitizing operation of the deep ultraviolet light source (S22).

According to the vehicular sanitization control device having the configuration of the above [5], a wasteful power consumption due to the operation of the sanitization function can be prevented when the vehicle has been parked for a long time.

[6] A vehicular sanitization control system, including:
the vehicular sanitization control device according to the above [1];
a vehicular battery mounted on a vehicle; and
a solar panel mounted on the vehicle, in which
the control unit switches a supply source of a power supplied to the deep ultraviolet light sources to the vehicular battery in a case that an ignition of the vehicle is in an on state (S12), and switches the supply source of the power supplied to the deep ultraviolet light source to the solar panel in a case that the ignition of the vehicle is in an off state (S13).

According to the vehicular sanitization control system having the configuration in the above [6], when the engine of the vehicle is stopped, the supply source of the power supplied to the deep ultraviolet light source is switched to the internal power source, so that the dead battery of the vehicular battery can be prevented. When the engine of the vehicle is operating and a vehicular generator or the like can be used, a source power consumption from the internal power source can be suppressed by switching the supply source of the power to an output of the vehicular battery or the like having a sufficient capacity.

What is claimed is:

1. A vehicle comprising:
a vehicular battery; and
a vehicular sanitization control device;
wherein the vehicular sanitization control device includes:
a rechargeable internal power source that is other than and separate from the vehicular battery;
a deep ultraviolet light source;
a first display light source configured to display an operating state of the deep ultraviolet light source;
a second display light source configured to display a state of charge of the internal power source; and
a control unit configured to control a power supplied to the deep ultraviolet light source, a charging operation of the internal power source, and displays of the first display light source and the second display light source, respectively, and
wherein the control unit switches a supply source of a power supplied to the deep ultraviolet light source to the vehicular battery based on an ignition of the vehicle transitioning from an off state to an on state, and switches the supply source of the power supplied to the deep ultraviolet light source to the rechargeable internal power source based on the ignition of the vehicle transitioning from the on state to the off state.

2. The vehicle according to claim 1, further comprising:
a solar panel, wherein
the solar panel is configured to be connected to a charging circuit of the internal power source.

3. The vehicle according to claim 1, wherein
the control unit includes a wireless communication unit configured to perform wireless communication with a wireless remote control unit, and
in response to a change in a state of the wireless remote control unit, the control unit controls an operation of supplying the power to the deep ultraviolet light source.

4. The vehicle according to claim 1, wherein
the control unit includes a timer configured to limit a length of a time of a sanitizing operation of the deep ultraviolet light source.

5. The vehicle according to claim 1, further comprising:
a solar panel connected to and configured to charge the rechargeable internal power source,
wherein the control unit switching the supply source of the power supplied to the deep ultraviolet light source to the rechargeable internal power source, based on the ignition of the vehicle transitioning from the on state to the off state, comprises switching the supply source of the power supplied to the deep ultraviolet light source to a combination of the deep ultraviolet light source and the solar panel connected to the rechargeable internal power source.

6. The vehicle according to claim 1,
wherein the vehicular sanitation control device is arranged inside of a cabin of the vehicle,
wherein the deep ultraviolet light source comprises a plurality of deep ultraviolet light emitting diodes (LEDs),
wherein a first one of the plurality of deep ultraviolet LEDs are arranged at a ceiling of the cabin above at least one of seats in the cabin of the vehicle,
wherein a second one of the plurality of deep ultraviolet LEDs is separate from the first one of the plurality of deep ultraviolet LEDs and is arranged at least at one of a door of the vehicle and a luggage compartment of the vehicle, and
wherein the ceiling of the cabin of the vehicle comprises a lamp configured to emit a visible light to the cabin of the vehicle.

7. The vehicle according to claim 1,
wherein the control unit is further configured to switch on the supply source of the power supplied to the deep ultraviolet light source, such that the deep ultraviolet light source is supplied with the power, in response to detecting that a state of the ignition of the vehicle is in the off state.

8. The vehicle according to claim 1, further comprising:
a housing;
a connector portion; and
a wire harness,
wherein the connector portion includes the control unit and the internal power source,
wherein the connector portion is housed in the housing,
wherein the deep ultraviolet light source, the first display light source, and the second display light source are connected to the connector portion via the wire harness.

* * * * *